(12) United States Patent
Yamashita

(10) Patent No.: US 7,927,616 B2
(45) Date of Patent: Apr. 19, 2011

(54) PESTICIDE COMPOSITIONS AND METHODS FOR THEIR USE

(75) Inventor: Thomas T. Yamashita, Turlock, CA (US)

(73) Assignee: Thomas T. Yamashita, Turlock, CA (US)

( * ) Notice: Subject to any disclaimer, the term of this patent is extended or adjusted under 35 U.S.C. 154(b) by 613 days.

(21) Appl. No.: 10/759,788

(22) Filed: Jan. 16, 2004

(65) Prior Publication Data

US 2005/0158355 A1 Jul. 21, 2005

(51) Int. Cl.
*A01N 25/32* (2006.01)

(52) U.S. Cl. .............. 424/406; 71/54; 71/57; 71/64.08; 71/64.1; 424/405; 424/633; 424/639; 424/641; 424/646; 424/676; 424/677; 514/649; 514/383

(58) Field of Classification Search .................. 424/405
See application file for complete search history.

(56) References Cited

U.S. PATENT DOCUMENTS

| | | | | |
|---|---|---|---|---|
| 3,161,497 A | * | 12/1964 | Amburn ................ | 504/318 |
| 3,231,365 A | * | 1/1966 | Wahlberg ............... | 71/1 |
| 3,514,516 A | * | 5/1970 | Summers ................ | 514/477 |
| 3,558,787 A | * | 1/1971 | Harmon ................ | 514/680 |
| 3,789,122 A | * | 1/1974 | Klopping .............. | 514/186 |
| 4,018,926 A | * | 4/1977 | Wommack, Jr. ......... | 514/311 |
| 4,976,767 A | * | 12/1990 | Kinnersley et al. ....... | 71/26 |
| 5,453,277 A | * | 9/1995 | McCoy ................ | 424/408 |
| 5,549,729 A | | 8/1996 | Yamashita | |
| 5,582,627 A | | 12/1996 | Yamashita | |
| 5,696,094 A | | 12/1997 | Yamashita | |
| 5,797,976 A | | 8/1998 | Yamashita | |
| 6,083,293 A | * | 7/2000 | Bath ................... | 71/16 |
| 6,165,245 A | | 12/2000 | Yamashita | |
| 6,254,654 B1 | * | 7/2001 | Van Barneveld ......... | 71/8 |
| 6,309,440 B1 | | 10/2001 | Yamashita | |
| 6,318,023 B1 | | 11/2001 | Yamashita | |
| 6,336,772 B1 | | 1/2002 | Yamashita | |
| 6,383,245 B1 | | 5/2002 | Yamashita | |
| 6,475,258 B1 | | 11/2002 | Yamishita | |
| 6,524,600 B2 | | 2/2003 | Yamashita | |
| 6,669,879 B1 | * | 12/2003 | Spengler et al. .......... | 264/112 |
| 2007/0134284 A1 | * | 6/2007 | Parker ................ | 424/410 |

* cited by examiner

*Primary Examiner* — Neil Levy
(74) *Attorney, Agent, or Firm* — Bozicevic, Field & Francis LLP; Bret E. Field; Glenn J. Foulds

(57) ABSTRACT

Pesticide compositions and methods for their use are provided. Embodiments of the subject pesticide compositions include a pesticide and an assimilable carbon skeleton energy component. Embodiments of the subject compositions may include a pesticide and one or more of a macronutrient component, micronutrient component, vitamin/cofactor component and a complexing agent. Also provided are methods that include preparing an assimilable carbon skeleton energy containing-pesticide composition and methods for administering an assimilable carbon skeleton energy containing-pesticide composition to a plant. Kits for use in practicing the subject invention are also provided. The subject pesticide compositions find use in a variety of different applications, and are particularly suited for use in at least mollifying pesticide-induced phytotoxicity of a plant.

14 Claims, No Drawings

PESTICIDE COMPOSITIONS AND METHODS FOR THEIR USE

FIELD OF THE INVENTION

The field of this invention is agriculture, particularly pesticide compositions used in agriculture.

BACKGROUND OF THE INVENTION

Many pesticides (insecticides, bactericides and fungicides) used in agriculture impart phytotoxic responses, i.e., subtle to distinct hindrances to the physiological functions of various plant species. Such pesticides may be referred to as phytotoxicants. In rendering a phytotoxic response in a plant, the efficacy of the pesticide may become compromised. For example, when the pesticide sodium fluoaluminate (common name cryolite, brand name KRYOCIDE) is sprayed onto actively growing vines, trees or vegetables, reduced metabolic activity can be observed for extended periods of time—which may exceed ten to fourteen consecutive days following the pesticide application. Although the targeted pest caterpillars may be controlled by the application of the sodium fluoaluminate, the phytotoxicity of the sodium fluoaluminate weakens the plant, predisposing it to both physical and biological stresses. Sodium fluoaluminate-induced phytoxocity is but one example, as pesticide phytotoxicity can be observed with the application of many different pesticides. For example, the fungicide chlorothalonil (brand name BRAVO) possesses broad spectrum fungicidal capabilities. However, chlorothalonil has been observed to incite physiological pesticide-induced phytotoxicity.

Other repercussions of pesticide induced phytotoxicity may occur. For example, while application of pesticides may protect the pesticide-treated plant from the target pest or pathogen, the health of the treated plants may be compromised, in many instances predisposing the plants to the next wave of pests Furthermore, phytotoxicity limits the range of plant groups for which a phytotoxic-inducing pesticide may be registered with the U.S. Environmental Protection Agency (EPA), thereby not only limiting market size for a pesticide manufacturer but also limiting the number of pesticides available to farmers and the like to combat pests. Furthermore, phytotoxicity may oftentimes be subtle and observed indirectly, e.g., by the need to use higher rates of pesticide to achieve satisfactory pesticide performance. In other words, phytotoxicity may compromise a plant's natural resistance such that additional, supplementary assistance via additional pesticide becomes necessary. However, the degree and number of restrictions promulgated by regulatory agencies responsible for pesticide usage, e.g., the U.S. EPA and the Department of Agriculture, and the like, are increasing and moving towards lowered rates of pesticides used, less frequency of pesticide use, etc. Still further, pesticide-induced phytotoxicity has been observed to negatively impact yield and quality of the treated plants to which such phytotoxic pesticides have been applied, thus further economically affecting farmers and the like.

Attempts have been made to address pesticide induced phytotoxicity issues. However, these attempts have not been wholly satisfactory. For example, naturally-derived fungicides were once thought to possess non-phytotoxic chemistry, but resultant phytotoxicity has since been observed with these pesticides as well. For example, many such naturally-derived fungicides are derived from mushroom fungal species and are collectively known as Strobylurines. One such member, Azoxystrobin (brand names Abound, Quadris) possess broad spectrum fungicide capability, but also imparts phytotoxic reactions when sprayed, for example, onto apples.

To be successful, current and future agricultural ventures will continue to require the use of pesticides. Accordingly, there continues to be an interest in the development and use of pesticides that are effective at addressing the target pest and/or pathogen of interest, but which at least mollifies the phytotoxic responses of the pesticide treated-plant. Of particular interest are such pesticide compositions that may be effectively used at relatively low rates and which provide effective crop performance.

SUMMARY OF THE INVENTION

Pesticide compositions and methods for their use are provided. Embodiments of the subject pesticide compositions include a pesticide and an assimilable carbon skeleton energy component. Embodiments of the subject compositions may include a pesticide and one or more of a macronutrient component, micronutrient component, vitamin/cofactor component and a complexing agent. Also provided are methods that include preparing an assimilable carbon skeleton energy containing-pesticide composition and methods for administering an assimilable carbon skeleton energy containing-pesticide composition to a plant. Kits for use in practicing the subject invention are also provided. The subject pesticide compositions find use in a variety of different applications, and are particularly suited for use in at least mollifying pesticide-induced phytotoxicity of a plant.

DETAILED DESCRIPTION OF THE INVENTION

Pesticide compositions and methods for their use are provided. Embodiments of the subject pesticide compositions include a pesticide and an assimilable carbon skeleton energy component. Embodiments of the subject compositions may include a pesticide and one or more of a macronutrient component, micronutrient component, vitamin/cofactor component and a complexing agent. Also provided are methods that include preparing an assimilable carbon skeleton energy containing-pesticide composition and methods for administering an assimilable carbon skeleton energy containing-pesticide composition to a plant. Kits for use in practicing the subject invention are also provided. The subject pesticide compositions find use in a variety of different applications, and are particularly suited for use in at least mollifying pesticide-induced phytotoxicity of a plant.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

In further describing the subject invention, the subject pesticide compositions are described first in greater detail, followed by a review of the subject methods for preparing exemplary pesticide compositions according to the subject invention and methods of using the subject compositions to treat plant. Finally, kits for use in practicing the subject methods are described.

Pesticide Compositions

As summarized above, the subject invention provides pesticide compositions that at least reduce or mollify pesticide-induced phytotoxicity of a plant brought about by administration of a phytotoxic inducing pesticide (i.e., a phytotoxicant) to the plant. Phytotoxicity may be characterized broadly as plant injury and may manifest or express itself in a number of ways including subtle and/or obvious symptoms. For example, symptoms may include compromised physical and/or physiological activity or function of one or more aspects of a plant and may range from minor leaf speckling to plant death. Phytotoxicity symptoms may include, but are not limited to, chlorosis, necrosis, burning, leaf speckling or banding, leaf drop, fruit spotting, distortion of new growth, stunting of growth, cessation of growth, discoloration (e.g., yellowing of the leaves (soaps)), root injury (e.g., poor root development or growth), puckering (xylene injury), tip browning, plant death, and the like. For example, phytotoxicity may result in a reduction or compromise in a plant's metabolic activity, such as manifested as adversely affecting (e.g., stunting) plant growth, e.g., phytotoxicity may be observed as an adverse effect on a plant's overall vigor and growth.

The subject compositions combine a phytotoxic inducing pesticide or a pesticide at least suspected of inducing phytotoxicity in a plant, and at least one phytotoxicity-mollifying or reducing component. When combined with a pesticide at least suspected of being a phytotoxic inducing pesticide, the at least one phytotoxic reducing component mollifies or "buffers" the magnitude or in certain instances eliminates phytotoxicity. Embodiments of the subject pesticide compositions are assimilable carbon skeleton energy component-containing pesticide compositions and as such include a pesticide and an assimilable carbon skeleton energy component.

Other phytotoxic reducing components that may be included in the subject pesticide compositions include, but are not limited to, one or more micronutrients component, a macronutrient component, a vitamin/cofactor component, and a complexing agent. Each of these components is described separately in greater detail below.

The inventor of the subject invention has discovered that the subject pesticide compositions (i.e., pesticide compositions that include one or more of: an assimilable carbon skeleton energy component, a macronutrient component, a micronutrient component, a vitamin/cofactor component and a complexing agent) provide unexpected, beneficial results when administered to a plant. More specifically, the inventor of the subject invention has realized that, when applied to a plant, the subject pesticide compositions provide subtle to significant increases in a plant's protection from pesticide-induced phytotoxicity, relative to the administration of a pesticide alone or rather without any of the additional phytotoxic-reducing components, where in certain instances phytotoxic effects are completely eliminated.

Pesticide

Any suitable pesticide(s) may be employed in the subject compositions. By pesticide is meant broadly to include any agent that affects the mortality or behavior of a target organism and includes, but is not limited to, insecticides, acaracides, miticides, fungicides, bactericides, herbicides, antibiotics, antimicrobials, nemacides, rodenticides, entomopathogens, phermones, attractants, plant growth regulators, insect growth regulators, chemosterilants, repellents, viruses and phagostimulents. Examples of these pesticides are known to those skilled in the art, and many are readily commercially available. Pesticides employed in the subject invention may be known to be phytotoxic or may be at least suspected of being phytotoxic. Pesticides employed in the subject compositions may be in any suitable form, e.g., may be in solid or liquid form, may be an organic pesticide, may be an inorganic pesticide, and the like.

The pesticides employed in the subject invention may be a naturally occurring, derived from natural materials or may be non-naturally occurring. The pesticide compositions may include a single pesticide or a plurality of pesticides. Where a subject pesticide composition includes a plurality of pesticides, the number of different pesticides in the composition may range from about 1 to about 10, e.g., from about 1 to about 7, e.g., from about 1 to about 5, e.g., from about 1 to about 4. In certain embodiments, at least one of the pesticides employed may be a small molecule pesticide, where by small molecule is meant that the molecule has a size that does not exceed about 10 kDa, and in certain embodiments does not exceed about 5 kDa.

As noted above, synthetic or man-made pesticides may also be employed in the subject compositions. Such synthetic pesticides include, but are not limited to organochlorines, organophosphates, organosulfurs, botanicals, carbamates, neonicotinyls (which include chloronicotinyls), antibiotics, dicarboximides, phenylamines, benzimidazoles, triazoles, strobylurines, imides, amides and pyrethroids.

| Pesticide Family | Pesticide Use | Trade Name Examples |
|---|---|---|
| Organophospahtes | Insecticide | Malathion, Diazinon, Lorsban, Phosmet |
| Organosulfurs | Miticide | Omite |
| Carbamates | Insecticide | Sevin, Furadan, Vydate |

-continued

| Pesticide Family | Pesticide Use | Trade Name Examples |
| --- | --- | --- |
| Botanicals | Insecticide | Nicotine, Sabadilla, Limonene, Pyrethrum |
| Synthetic Pyrethroids | Insecticide | Pounce, Baythroid |
| Antibiotics | Microbialcide | Agrimycin, Tetracycline |
| Inorganics | Fungicide | Copper, Sulfur, Kocide |
| ethylene(bis)dithiocarbamates ("EBDTs") | Fungicide | Dithane, Maneb, Farmaneb, Manesan, Manex, Manzate, Nereb, Newspor, Thiram |
| Dicarboximide | Fungicide | Captan, Captec, Difolatan |
| Benzimidazoles | Fungicide | Benlate, Topsin, TBZ |
| Phenylamines | Fungicide | Ridomil |
| Triazoles | Fungicide | Bayleton, Orbit, Rally, Tilt |
| Organophosphates | Fungicide | Aliette, Nutri-Phite |
| Imides | Fungicide | Rovral, Ronilan |
| Strobylurines | Fungicide | Abound |
| Amide | Herbicide | Gallery, Kerb |
| Phosphono Amino Acid | Herbicide | Roundup |
| Substituted Aromatics | Fungicide | Bravo, Botran, Terraclor |
| Inorganics | Insecticide | Kryocide |

The pesticides are present in the subject composition in an amount sufficient to perform their required pesticide task. The particular amount of a given pesticide in a given composition may vary depending on a variety of factors such as the particular pesticide, the particular target organism, the plant to be treated, etc. In certain embodiments, the pesticide component of the subject compositions ranges from about 0.01% to about 15.0% w/w of the composition, e.g., from about 0.05% to about 10.0% w/w of the composition, e.g., from about 0.08% to about 8.0% w/w of the composition.

Assimilable Carbon Energy Component

Embodiments of the subject compositions also include an assimilable carbon skeleton energy (ACSE) component. ACSE components that find use in the subject compositions are carbon-containing substances which provide a readily plant-assimilable source of both carbon and energy for the plant. Accordingly, the function of this component is to supply carbon skeleton for synthesis of proteins and other plant molecules and to supply energy for plant metabolism such that an ACSE component, when suitably assimilated or absorbed by the plant, may provide a source of energy and also a source of carbon skeleton from which, for example, proteins may be synthesized by the plant. As the carbon skeleton energy components are assimilable by a plant, they are water soluble components so as to be easily assimilable by a plant.

Embodiments include an ACSE component that is a $C_2$ to $C_{14}$, e.g., $C_4$ to $C_8$ compound or polymer thereof, e.g., a polymer in which the monomeric units $C_2$ to $C_{14}$ compounds, such as a polysaccharide. The ACSE component may be a single carbon containing compound or a composition of two or more different carbon containing or organic compounds. Compounds and compositions capable of serving as a ACSE component include, but are not limited to: complex organic compositions, such as molasses (e.g. cane, sugar beet, sorghum, etc.), whey, corn steep liquor, grape syrup, maple syrup, corn syrup, etc; sugars, e.g. sucrose, fructose, glucose, lactose, galactose, dextrose, maltose, raffinose, ribose, ribulose, xylulose, xylose, amylose, arabinose, etc.; sugar phosphates, e.g. fucose-P, galactose-P, glucose-P, lactose-P, maltose-P, mannose-P, ribose-P, ribulose-P, xylose-P, xylulose-P, etc.; sugar alcohols, e.g. adonitol, sorbitol, mannitol, maltitol, ribitol, galactitol, glucitol, etc.; organic acids, e.g. gluccuronic acid, alpha ketoglutaric acid, galactonic acid, glucaric acid, gluconic acid, pyruvic acid, polygalacturonic acid, citric acid, succinic acid, malic acid, isocitric acid, folic acid, etc.; nucleotides and bases, e.g. adenosine, adenosine-P, uridine, uridine-P, thymine, thymine-P, cytosine, cytosine-P, guanine, guanine-P, etc.; and amino acids, e.g. glycine, alanine, leucine, isoleucine, asparagine, tyrosine, phenylalanine, serine, cysteine, valine, proline, methionine, glutamine, threonine, lysine, aspartic acid, glutamic acid, arginine, and the like.

Of interest are sucrose ACSE components and corn syrup ACSE components. Also of interest is molasses. For example, in those embodiments that employ molasses, the molasses may be obtained from a number of commercial sources, including cane molasses, etc., where commercial sources of molasses include: Westway Terminal, Stockton Calif.; PM Ag, Stockton, Calif.; and the like.

The ACSE component of the subject compositions are present in an amount suitable to at least reduce the phytotoxic effects of at least the pesticide used in the composition, where the ACSE component may provide for such reduced phytotoxicity alone or may function in combination with other components in a composition. Accordingly, embodiments include an amount of ACSE component present in a subject composition in a pesticide phytotoxicity-reducing amount. The particular amount of a given ACSE component present in a given composition depends on a variety of factors such as the particular plant to which the composition is to be administered, the particular ACSE component employed, the particular pesticide(s) employed, and the like. In many embodiments, the amount of ACSE component in a pesticide composition may range from about 0.1% to about 20% w/w, e.g., from about 0.1% to about 18% w/w, e.g., from about 0.3% to about 16.0% w/w, e.g., from about 1.0% to about 10.0% w/w.

Water

The subject compositions may be aqueous or non-aqueous compositions, i.e., may be in solid form, semi-solid form or liquid form. In embodiments that include an amount of liquid, the amount of liquid will vary such that the viscosity of a given pesticide composition may vary and range from low to high. For example, viscosities may range from about 1 centipoise ("cp") to about 50,000 cp, e.g., from about 10 cp to about 25,000 cp, e.g., from about 20 cp to about 15,000 cp. In those embodiments in which the compositions are aqueous compositions, they further include a suitable amount of water. The amount of water present in the composition may vary and may range from about 15% to about 99.9% w/w of water, e.g., about 25% to about 85% w/w of water, e.g., about 40% to about 70% w/w of water.

The water used in the subject composition may be obtained from any suitable source, e.g., a municipal water source and the like. In certain embodiments, purified water is employed, e.g., to dilute pesticide concentrates to provide application-ready pesticide formulations, to assist in mixing the composition components, etc. For example, water utilized to prepare application-ready pesticide compositions in accordance with this invention may be purified to have a total dissolved solids (TDS) content of about 1 to about 500 ppm in certain embodiments.

Additional Components

Embodiments of the subject compositions may also include one or more additional components such as, but not limited to, one or more macronutrient components and/or one or more micronutrient components and/or one or more vitamin/cofactor components and/or one or more complexing agents. Other components such as buffers, surfactants, wetting agents, spreaders, emulsifiers, viscosity regulators, diluents, dispersing agents, foaming agents and foaming suppressants, penetrants, stickers, correctants and attractants, and the like may also be employed. For example, embodiments of the pesticide composition may include pesticide compositions that have a pH that ranges from about 1 to about 12, e.g., from about 3 to about 9, e.g., from about 5 to about 8. Accordingly, a suitable buffer may be employed to maintain a specific pH. Any suitable buffer may be used, e.g., phosphate, amino acid, polyhydroxy organic acid, and the like.

As noted above, a surfactant may be used. The term "surfactant" is used herein in its conventional sense to refer to a compound that effects reduction in the surface tension in a fluid. Surfactants may be used to increase the spreading and wetting properties of a pesticide composition. For example, surfactants may be used to increase spreading, coverage and penetration of hard and wet soils to provide a more uniform distribution of a pesticide composition.

Examples of surfactants that may be employed in the subject pesticide compositions include anionic, cationic, amphoteric and nonionic surfactants. For example, nonionic surfactants that may be employed in certain embodiments include organosilicone surfactants. A particular organosilicone surfactant that may be used in certain embodiments is a surfactant that includes a combination of polyalkyleneoxide modified heptamethyltrisiloxane combined with allyloxypolyethyleneglycol methyl ether (e.g., available under the brand name SILWET L-77® surfactant available from GE Silicones of West Virginia). Other surfactants may also be used. Other, exemplary surfactants that may be employed are included, but not limited to, those provided in the table below.

Other optional components are now described in greater detail.

Macronutrients

As noted above, the subject assimilable carbon skeleton energy component-containing pesticide compositions may also include one or more macronutrient components for plant nutrition and growth. As the macronutrient components are components that are used by a plant, they are typically water soluble components so as to be in a form that may be easily used by a plant. The subject compositions may include one or a plurality of macronutrient components.

Accordingly, the number of macronutrient components present in a composition may range from about 1 to about 15 or more, e.g., from about 1 to about 6, e.g., from about 2 to about 6.

The total amount of macronutrient component present in a given composition (whether one or a plurality of macronutrients) depends on a variety of factors such as the particular plant to which the composition is to be administered, the particular macronutrient component(s) employed, and the like. In many embodiments, the total amount of macronutrient component in the composition may range from about 0.0001% to about 0.5% w/w, e.g., from about 0.001% to about 0.3% w/w, e.g., from about 0.001% to about 0.2% w/w. Exemplary macronutrient components include, but are not limited to one or more of: N, P, K, Ca, Mg, S, Cl, Na, C, H, O. For example, certain embodiments may include one or more of the following exemplary macronutrient components R—ammonium nitrate, monoammonium phosphate, ammonium phosphate sulfate, ammonium sulfates, ammonium phosphatenitrate, diammonium phosphate, ammoniated single superphosphate, ammoniated triple superphosphate, nitric phosphates, ammonium chloride, aqua ammonia, ammonia-ammonium nitrate solutions, calcium ammonium nitrate, calcium nitrate, calcium cyanamide,

| Generic Name | Exemplary Brand Name | Chemical Name | Category |
|---|---|---|---|
| organosilicone spreader | Kinetic | Polyalkyleneoxide modified polydimethylsiloxane and nonionic surfactants | wetter/spreader/penetrant |
| nonionic spreader | Active Plus | Alkylarylpolyoxyethylene glycols plus free fatty acids | nonionic spreader |
| nonionic spreader | Ad-Wet | Nonylphenoxypoly(ethyleneoxy) ethanol, isopropyl alcohol 2-methoxy ethanol, oleic acid 80% | spreader/penetrant |
| nonionic spreader | Amway All-Purpose Spray Adjuvant | alkyl aryl polyalkoxylated alcohols | wetting agent |
| nonionic spreader | Anchor | Cottonseed oil, alkylphenoxy polyethoxy ethanols | sticker/spreader |
| buffering agent | Balance | Alkyl aryl phosphoric acid ester, phosphoric acid | buffer/wetting agent |
| nonionic spreader | Bio-Film | Alkylarylpolyoxyethylene, fatty acids, glycol ethers, di-alkyl benzene, dicarboxylate, isopropanol | spreader/sticker |
| nonionic spreader | First Choice Spreader Sticker | Alkylarylpolyoxyethylene glycol, isopropyl alcohol | spreader/sticker |
| nonionic spreader | Frigate | Fatty amine ethyoxylate | adjuvant |
| anti-foam agent | No Foam Adjuvant | Nonyl phenoxy polyethoxy ethanol polydimethyl/siloxane | spreader/activator |
| nonionic spreader | Nu-Film-P | Poly-1-p-menthene | spreader/sticker | sodium nitrate, urea, urea-formaldehyde, urea-ammonium nitrate solution, nitrate of soda potash, potassium nitrate, amino acids, proteins, nucleic acids P—superphosphate (single, double and/or triple), phosphoric acid, ammonium phosphate, ammonium phosphate sulfate, ammonium phosphate nitrate, diammonium phosphate, ammoniated single superphosphate, ammoniated single superphosphate, ammoniated triple superphosphate, nitric phosphates, potassium pyrophosphates, sodium pyrophosphate, nucleic acid phosphates K—potassium chloride, potassium sulfate, potassium gluconate, sulfate of potash magnesia, potassium carbonate, potassium acetate, potassium citrate, potassium hydroxide, potassium manganate, potassium phosphate, potassium molybdate, potassium thiosulfate, potassium zinc sulfate Ca—calcium ammonium nitrate, calcium nitrate, calcium cyanamide, calcium acetate, calcium acetylsalicylate, calcium borate, calcium borogluconate, calcium carbonate, calcium chloride, calcium citrate, calcium ferrous citrate, calcium glycerophosphate, calcium lactate, calcium oxide, calcium pantothenate, calcium proprionate, calcium saccharate, calcium sulfate, calcium tartrate Mg—magnesium oxide, dolomite, magnesium acetate, magnesium bensoate, magnesium bisulfate, magnesium borate, magnesium chloride, magnesium citrate, magnesium nitrate, magnesium phosphate, magnesium salicylate, magnesium sulfate S—ammonium sulfate, ammonium phosphate sulfate, calcium sulfate, potassium sulfate, magnesium sulfate, sulfuric acid, cobalt sulfate, copper sulfate, ferric sulfate, ferrous sulfate, sulfur, cysteine, methionine Micronutrients As noted above, the subject assimilable carbon skeleton energy component-containing pesticide compositions may also include one or more micronutrient components for plant nutrition and growth. As the micronutrient components are components that are used by a plant, they are typically water soluble components so as to be in a form that may be easily used by a plant. The subject compositions may include one or a plurality of micronutrient components. Accordingly, the number of macronutrient components present in a composition may range from about 1 to about 60 or more, e.g., from about 3 to about 55, e.g., from about 4 to about 50.

The total amount of micronutrient component present in a given composition (whether one or a plurality of micronutrients) depends on a variety of factors such as the particular plant to which the composition is to be administered, the particular micronutrient component(s) employed, and the like. In many embodiments, the total amount of micronutrient component in the composition may range from about 0.00000001% to about 0.1% w/w, e.g., from about 0.00000001% to about 0.5% w/w, e.g., from about 0.00000001% to about 0.005% w/w. Exemplary micronutrient components include, but are not limited to:

Zn—zinc oxide, zinc acetate, zinc bensoate, zinc chloride, zinc citrate, zinc nitrate, zinc salicylate, ziram.

Fe—ferric chloride, ferric citrate, ferric fructose, ferric glycerophosphate, ferric nitrate, ferric oxide (saccharated), ferrous chloride, ferrous citrate ferrous fumarate, ferrous gluconate, ferrous succinate.

Mn—manganese acetate, manganese chloride, manganese nitrate, manganese phosphate.

Cu—cupric acetate, cupric butyrate, cupric chlorate, cupric chloride, cupric citrate, cupric gluconate, cupric glycinate, cupric nitrate, cupric salicylate, cuprous acetate, cuprous chloride.

B—calcium borate, potassium borohydride, borax, boron trioxide, potassium borotartrate, potassium tetraborate, sodium borate, sodium borohydride, sodium tetraborate.

Mo—molybdic acid, calcium molybdate, potassium molybdate, sodium molybdate.

Co—cobaltic acetate, cobaltous acetate, cobaltous chloride, cobaltous oxalate, cobaltous potassium sulfate, cobaltous sulfate.

Vitamins and Cofactors

As noted above, the subject assimilable carbon skeleton energy component-containing pesticide compositions may also include one or more vitamin/cofactor components. As the vitamin/cofactor components are components that are used by a plant, they are typically water soluble components so as to be in a form that may be easily used by a plant. The subject composition may include one or a plurality of vitamin/cofactor components. Accordingly, the number of vitamin/cofactor components present in a composition may range from about 1 to about 20 or more, e.g., from about 3 to about 15, e.g., from about 5 to about 12.

The total amount of vitamin/cofactor component present in a given composition (whether one or a plurality of vitamin/cofactor components) depends on a variety of factors such as the particular plant to which the composition is to be administered, the particular vitamin/cofactor component(s) employed, and the like. In many embodiments, the total amount of vitamin/cofactor component in the composition may range from about 0.00000001% to about 0.1% w/w, e.g., from about 0.0000001% to about 0.05% w/w, e.g., from about 0.000001% to about 0.01% w/w. Exemplary vitamin/cofactor components include, but are not limited to:

Thiamine—thiamine pyrophosphate, thiamine monophosphate, thiamine disulfide, thiamine mononitrate, thiamine phosphoric acid ester chloride, thiamine phosphoric acid ester phosphate salt, thiamine 1,5 salt, thiamine triphosphoric acid ester, thiamine triphosphoric acid salt, yeast, yeast extract.

Riboflavin—riboflavin acetyl phosphate, flavin adenine dinucleotide, flavin adenine mononucleotide, riboflavin phosphate, yeast, yeast extract.

Nicotinic acid—nicotinic acid adenine dinucleotide, nicotinic acid amide, nicotinic acid benzyl ester, nicotinic acid monoethanolamine salt, yeast, yeast extract, nicotinic acid hydrazide, nicotinic acid hydroxamate, nicotinic acid-N-(hydroxymethyl)amide, nicotinic acid methyl ester, nicotinic acid mononucleotide, nicotinic acid nitrile.

Pyridoxine—pyridoxal phosphate, yeast, yeast extract.

Folic acid—yeast, yeast extract, folinic acid.

Biotin—biotin sulfoxide, yeast, yeast extract, biotin 4-amidobenzoic acid, biotin amidocaproate N-hydroxysuccinimide ester, biotin 6-amidoquinoline, biotin hydrazide, biotin methyl ester, d-biotin-N-hydroxysuccinimide ester, biotin-maleimide, d-biotin p-nitrophenyl ester, biotin propranolol, 5-(N-biotinyl)-3 aminoallyl)-uridine 5'-triphosphate, biotinylated uridine 5'-triphosphate, N-e-biotinyl-lysine.

Pantothenic acid—yeast, yeast extract, coenzyme A.

Cyanocobalamin—yeast, yeast extract.

Phosphatidylcholine—soybean oil, eggs, bovine heart, bovine brain, bovine liver, L-a-phosphatidylcholine, B-acetyl-g-O-alkyl, D-a-phosphatidylcholine (PTCn), B-acetyl-g-O-hexadecyl, DL-a-PTCh, B-acetyl-g-O-hexadecyl, L-a-PTCh, B-acetyl-g-O-(octadec-9-cis-e-nyl), L-a-PTCh, B-arachidonoyl, g-stearoyl, L-a-PTCh, diarachidoyl, L-a-PTCh, dibehenoyl(dibutyroyl, dicaproyl, dicapryloyl, didecanoyl, dielaidoyl, 12 diheptadecanoyl, diheptanoyl), DL-a-PTCh dilauroyl, La-PTCh dimyristoyl(dilauroyl, dilinoleoyl, dinonanoyl, dioleoyl, dipentadecanoyl, dipalmitoyl, distearoyl, diundecanoyl, divaleroyl, B-elaidoyl-a-palmitoyl, B-linoleoyl-a-palmitoyl)DL-a-PTCh di-O-hexadecyl(dioleoyl, dipalmitoyl, B—O-methyl-g-O-hexadecyl, B-oleoyl-g-O-hexadecyl, B-palmitoyl-g-O-hexadecyl), D-a-PTCh dipalmitoyl, L-a-PTCh, B—O-methyl-g-O-octadecyl, L-a-PTCh, B-(NBD-aminohexanoyl)-g-pal-mitoyl, L-a-PTCh, B-oleoyl-g-O-palmitoyl(stearoyl), L-a-PTCh, B-palmitoyl-g-oleoyl, L-a-PTCh, B-palmitoyl-a-(pyren 1-yl)hexanoyl, L-a-PTCh, B(pyren-1-yl)-decanoyl-g-palmitoyl, L-a-PTCh, B-(pyren-1-yl)-hexanoyl-g-palmitoyl, L-a-PTCh, B-stearoyl-g-oleoyl.

Inositol—inositol monophosphate, inositol macinate, myo-inositol, epi-inositol, myo-inositol 2,2'anhydro-2-c-hydroxymethyl(2-c-methylene-my-oinositol oxide), D-myo-inositol 1,4-bisphosphate, DL-myo-inositol 1,2-cyclic monophosphate, myo-inositol dehydrogenase, myo-inositol hexanicotinate, inositol hexaphosphate, myo-inositol hexasulfate, myo-inositol 2-monophosphate, D-myo-inositol 1-monophosphate, DL-myo-inositol 1-monophosphate, D-Myo-inositol triphosphate, scyllo-inositol.

PABA—m-aminobenzoic acid, O-aminobenzoic acid, p-aminobenzoic acid butyl ester, PABA ethyl ester, 3-ABA ethyl ester.

Complexing Agents

As noted above, the subject assimilable carbon skeleton energy component-containing pesticide compositions may also include one or more complexing agents. A complexing agent is an agent that aids in the solubilization of other components in the composition which otherwise may precipitate and become non-assimilable or difficulty assimilable. For example, a complexing agent such as citric acid, humic acids, lignosulfonate, etc. may serve to tie up ions such as iron and other ions and prevent them from forming precipitates such that a complexing agent may be an agent that is capable of complexing with a metal ion. In some cases, e.g. with EDTA, this complexing is by way of a process of chelation. The component, e.g., macronutrient or micronutrient, so complexed nevertheless remains assimilable. As such, complexing agents may be described as agents which act to facilitate transfer of other components into the cell structure of a plants. As the complexing agents are used by a plant, they are typically water soluble agents so as to be in a form that may be easily used by a plant.

The subject composition may include one or a plurality of complexing agents. Accordingly, the number of complexing agents present in a composition may range from about 1 to about 35 or more, e.g., from about 1 to about 20, e.g., from about 1 to about 10.

The total amount of complexing agent present in a given composition (whether one or a plurality of complexing agents) depends on a variety of factors such as the particular plant to which the composition is to be administered, the particular complexing agent(s) employed, and the like. In many embodiments, the total amount of complexing agent in the composition may range from about 0.01% to about 30% w/w, e.g., from about 0.1% to about 25% w/w, e.g., from about 1.0% to about 20% w/w. Exemplary vitamin/cofactor components include, but are not limited to: citric acid, lignosulfonates, e.g., Ca—, K—, Na—, and ammonium lignosulfonates, fulvic acid, ulmic acid, humic acid, amino acids, nucleic acids, ethylenediamin tetraacetatic acid (EDTA), diethylene triamine pentacetic acid (DTPA), nitrolotriacetic acid (NTA), ethylenediaminediacetate (EDDA), ethylenediaminedi(o-hydroxyphenylacetic) acid (EDDHA), hydroxyethylethylenediaminetriacetic acid (HEDTA), cyclohexane diamine tetraacetic acid (CDTA), and the like Naturally occurring chelating agents may also be employed. By naturally occurring chelating agent is meant that the chelating agent is a chelating agent that occurs in nature, i.e. not an agent that has been first synthesized by human intervention. The naturally occurring chelating agent may be a low molecular weight chelating agent, where by low molecular weight chelating agent is meant that the molecular weight of the chelating agent does not exceed about 200 daltons. In many embodiments, the molecular weight of the chelating agent is greater than about 100 daltons.

Naturally occurring low molecular weight chelating agents that may be used are microbial produced chelating agents, where by "microbial produced" is meant that the chelating agent is produced by a microbe, where the microbe is generally a bacterium or a fungus. In many embodiments, the chelating agents are citric acid cycle intermediates and derivatives thereof. Specific chelating agents of interest include: malic acid, succinic acid, oxalacetic acid, ketoglutaric acid and citric acid and amino acids derived from citric acid cycle intermediates, such as glycine (75.1 daltons), alanine (89.1 daltons), serine (105.1 daltons), valine (117.2 daltons), threonine (119.1 daltons), cysteine (121.2 daltons), leucine (131.2 daltons), isoleucine (131.2 daltons), asparginine (132.1 daltons), glutamine (146.2 daltons), methionine (149.2 daltons), etc.

Accordingly, embodiments include compositions that may include a source of at least one naturally occurring chelating agent. By source is meant that the compositions may include the chelating agents or an entity or component that produces the chelating agents. In many embodiments, the source of chelating agents is a living or viable microbial source of chelating agents. For example, the microbial source may be a bacterial or fungal culture which produces the requisite chelating agents.

Exemplary Pesticide Compositions

As described above, embodiments of the subject pesticide compositions at least include a pesticide and an assimilable carbon skeleton energy component. However, certain embodiments include one or more additional components as described above. Plant formulations that include one or more components of the subject invention and which may be employed in the subject invention include, but are not limited to, those described in, and analogous to those described in, U.S. Pat. Nos. 5,797,976; 5,549,729 and 6,309,440, the disclosures of which are herein incorporated by reference. A particularly effective pesticide composition may include a pesticide and GREEN THUMB™ 1-0-2 plant constituent formulation. GREEN THUMB 1-0-2 is trademark of Fusion 360 of Turlock, Calif. for a plant constituent formulation. In general, GREEN THUMB 1-0-2 plant constituent formulation includes a carbon skeleton energy component, nitrogen (urea nitrogen and nitrate nitrogen), potassium ($K_2O$), calcium, magnesium, zinc, manganese and iron. Accordingly, GREEN THUMB 1-0-2 plant constituent formulation combined with a pesticide (e.g., Kryocide, Kocide, Bravo Weather Stik, Orbit, and the like), provides an effective pesticide composition that at least reduces pesticide phytotoxicity, as compared to administration of a pesticide alone to a plant.

Embodiments may include a sodium aluminofluoride pesticide (e.g., Kryocide). Accordingly, pesticide compositions that at least reduce pesticide phytotoxicity may include a sodium aluminofluoride pesticide and sucrose or may include a sodium aluminofluoride pesticide and GREEN THUMB. For example, an exemplary assimilable-carbon skeleton energy containing pesticide may include a sodium aluminofluoride pesticide (e.g., KRYOCIDE) at 15 lbs. per 100 gallons, 3 oz. Per 100 gallons of an organosilicone surfactant (e.g., SILWET L-77), and 25 lbs. per 100 gallons sucrose. Embodiments may also include a sodium aluminofluoride pesticide (e.g., KRYOCIDE) at 15 lbs. per 100 gallons, 3 oz. Per 100 gallons of an organosilicone surfactant (e.g., SILWET L-77), and GREEN THUMB 1-0-2 plant constituent formulation at 4 gallons per 100 gallons.

Embodiments may also include a copper hydroxide pesticide (e.g., KOCIDE). Accordingly, pesticide compositions that at least reduce pesticide phytotoxicity may include a copper hydroxide pesticide and sucrose or a copper hydroxide pesticide and GREEN THUMB 1-0-2 plant constituent formulation. For example, an exemplary assimilable-carbon skeleton energy containing pesticide may include a copper hydroxide pesticide (e.g., KOCIDE) at 10 lbs. per 100 gallons, 3 oz. Per 100 gallons of an organosilicone surfactant (e.g., SILWET L-77), and 25 lbs. per 100 gallons sucrose. Embodiments may also include a copper hydroxide pesticide (e.g., KOCIDE) at 15 lbs. per 100 gallons, 3 oz. Per 100 gallons of an organosilicone surfactant (e.g., SILWET L-77), and GREEN THUMB 1-0-2 plant constituent formulation at 4 gallons per 100 gallons.

Embodiments may also include a chlorothalonil pesticide (e.g., BRAVO WEATHER STIK). Accordingly, pesticide compositions that at least reduce pesticide phytotoxicity may include a chlorothalonil pesticide (e.g., BRAVO WEATHER STIK) and sucrose or a chlorothalonil pesticide (e.g., BRAVO WEATHER STIK) pesticide and GREEN THUMB 1-0-2 plant constituent formulation. For example, an exemplary assimilable-carbon skeleton energy containing pesticide may include a chlorothalonil pesticide (e.g., BRAVO WEATHER STIK) at 2 pints per 100 gallons, 3 oz. Per 100 gallons of an organosilicone surfactant (e.g., SILWET L-77), and 25 lbs. per 100 gallons sucrose. Embodiments may also include a chlorothalonil pesticide (e.g., BRAVO WEATHER STIK) at 2 pts. per 100 gallons, 3 oz. Per 100 gallons of an organosilicone surfactant (e.g., SILWET L-77), and GREEN THUMB 1-0-2 plant constituent formulation at 4 gallons per 100 gallons.

Embodiments may also include a propiconazole pesticide (e.g., ORBIT). Accordingly, pesticide compositions that at least minimize pesticide phytotoxicity may include a propiconazole pesticide (e.g., ORBIT) and sucrose or a propiconazole pesticide (e.g., ORBIT) and GREEN THUMB. For example, an exemplary assimilable-carbon skeleton energy containing pesticide may include a propiconazole pesticide (e.g., ORBIT) at 12 ounces per 100 gallons, 3 oz. Per 100 gallons of an organosilicone surfactant (e.g., SILWET L-77), and 25 lbs. per 100 gallons sucrose. Embodiments may also include a propiconazole pesticide (e.g., ORBIT) at 2 pts. per 100 gallons, 3 oz. Per 100 gallons of an organosilicone surfactant (e.g., SILWET L-77), and GREEN THUMB 1-0-2 plant constituent formulation at 4 gallons per 100 gallons.

Composition Preparation

In general, the pesticide compositions are prepared by combining a pesticide with one or more other components (e.g., an assimilable carbon skeleton energy component and/or a macronutrient component and/or a micronutrient component and/or a complexing agent), each in amounts sufficient to yield the desired pesticide compositions, where such amounts generally fall within the ranges provided above. For example, embodiments include combining a suitable, amount of a pesticide at least with a suitable amount of an assimilable carbon skeleton energy component. In certain embodiments, water is also combined with the pesticide and one or more other components to provide an aqueous pesticide composition.

The various components used to produce the subject pesticide compositions may be obtained from any convenient source and/or produced using conventional protocols known to those of skill in the art. For example, the water that is used to produce the subject compositions may be tap water obtained from any convenient water source, e.g. a municipal water district, where the water may be purified or otherwise treated, e.g. to remove certain undesirable agents that may be initially present therein. The various minerals may be obtained from any convenient source, e.g. commercial vendors.

In certain embodiments, a subject pesticide composition may be prepared in a mix tank (e.g., "or analogous mixing apparatus). For example, such embodiments may include tank mixing in a spray tank by combining a phytotoxic pesticide with an assimilable carbon skeleton energy component and/or a macronutrient component and/or a micronutrient component and/or a vitamin/cofactor component and/or a complexing agent in such a mixing apparatus or other analogous apparatus. In certain embodiments a tank mix may be prepared by combining a phytotoxicant with a combined mixture represented by GREEN THUMB 1-0-2, which includes an assimilable carbon skeleton energy component, a macronutrient component, a micronutrient component and a vitamin/cofactor component. In certain other embodiments, some or all of the components of the pesticide composition may be pre-formulated, i.e., provided to the end user in a pre-mixed form.

As noted above, one or more other components may also be included in the subject compositions (e.g., one or more buffers, surfactants, wetting agents, spreaders, emulsifiers, viscosity regulators, diluents, dispersing agents, foaming agents and foaming suppressants, penetrants, stickers, correctants, attractants, and the like). Accordingly, any other component is added to the compositions and mixed therewith. For example, in those embodiments where a surfactant is used, such may be added to a tank after all other components are added in order to minimize foam generation. Embodiments also include an anti-foam agent, e.g., Foambuster, and the like. Foambuster is the brand name of a dimethylpolysiloxane-containing anti-foaming agent available from Helena Development Lab and is designed to minimize or prevent foaming problems associated with some pesticides in water-based sprays. In such instances, an anti-foaming agent may be added to a tank prior to the addition of a surfactant.

Components of a given pesticide composition may be packaged separately or together at a manufacturing site and transported to a user for use. For example, a manufacturer, distributor, retail outlet, etc. may package specific components separately, with specific instructions for combining the components in suitable ratios to produce a pesticide composition for use that at least reduces pesticide phytotoxicity and/or instructions for using the pesticide composition on a plant. In such instances, a user may then receive the separately packaged components and instructions and combine the components together according to the instructions to provide a subject pesticide composition. Embodiments may also include packaged pesticide compositions wherein some or all of the component are mixed together (i.e., pre-formulated), e.g., at a manufacturing site, distributor, etc., such that some or all of the components are combined prior to packaging of the components. Such embodiments may include instructions for mixing one or more other components and/or for further processing and/or instructions for using the pesticide composition on a plant.

Methods

The subject pesticide compositions find use in a variety of applications where a plant is in need, or is suspected of being in need, of a pesticide. Accordingly, the subject compositions may be used on any number of different types of plants, e.g., any plant for which a particular pesticide used in the subject invention is registered with the Environmental Protection Agency's (EPA's) Office of Pesticide and/or an appropriate state agency.

Exemplary types of plants that may be treated using the subject compositions include, but are not limited to, cereal crops (e.g., Rice, Wheat, Corn, Barley, Oats, Sorghum, Rye, Millet, and the like); legumes (e.g., Soybean, Peanut, Beans, Broad Bean, Pea, Chickpea or Garbanzo, Black Eyed Pea, Lentil, Pigeon Pea, Guar, and the like); forage crops (e.g., Clover, Bird's Foot Trefoil, Vetch, Sweet Clover, Lespedeza, Lupine, Sorghum-Sudan, Kentucky Bluegrass, Timothy, Orchardgrass, Fescua, Bermudagrass, Dallisgrass & Bahiagrass, Ryegrass, Bentgrass and the like); stem and leaf crops (e.g., Sugar Cane, Artichoke, Asparagus, Broccoli, Brussels Sprouts, Cabbage, Celery, Chard, Chinese Cabbage, Collards, Endive, Lettuce, Parsley, Rhubarb, Spinach and the like); root crops (e.g., Potato, Cassave, Sweet Potato, Beets, Taro, Carrot, Horseradish, Jerusalem artichoke, Onion, Parsnip, Radish, Rutabaga, Salsify, Turnip, Yam, and the like); fruit and seed vegetables (e.g., Tomato, Eggplant, Curcurbits, Okra, Pepper, and the like); fruit and nut crops (e.g., Citrus, Grape, Banana, Apple, Stone Fruits, Blueberry, Brambles, Cranberry, Currant, Pear, Avocado, Cashew, Coconut, Date, Fig, Guava, Litchi, Maracuja, Mango, Olive, Papaya, Pineapple, Pomegranate, Almond, Brazil Nut, Filberts, Macadamia, Pecan, Pistachio, Walnuts, Sunflower and the like); beverage crops (e.g., Coffee, Tea, Cacao, Cola, Hops, and the like); oil, fat and wax crops (e.g., Safflower, Coconut, African Oilpalm, Castor Bean, Rape, Sesame, Sunflower, Linseed, Tung, Soybean, Camauba, Candelilla, Jojoba, and the like); spices, perfumes an flavorings (e.g., Black Pepper, Cinnamon, Clove, Vanilla, Mint, Oregana, Allspice, Anise, Angelica Oil, Mustard, Sage, Ginger, Rose Oil, Bergamot, Camphor, Cananga, Citronella Grass, Eucalyptus, Geranium Oil, Lavandula, Rosemary, Thyme, Turpentine, and the like); ornamentals, forest and fiber crops (e.g., Cotton, Flax, Hemp, Christmas Trees (various conifers), Ornamental Evergreens, Rose, Chrysanthemum, Carnation, Iris, Azalea, Rhododendron, and the like); and houseplants (various species).

In practicing the subject methods, a phytotoxic-reducing pesticide composition of the subject invention is applied to at least one of: the plant, a portion thereof and soil associated therewith. As such, the composition may be, in certain embodiments, applied to foliage of the plant, e.g., either the entire part of the plant which is above the soil level or a portion thereof, e.g., fruit, leaves, etc. In other embodiments, the composition may be applied to soil associated with the plant, i.e., soil proximal to the plant in which the plant is growing, i.e., soil that is contacted by the roots of the plant or from which the plant's roots ultimately obtain nutrients and/or water.

Prior to contacting a pesticide composition with a plant, the pesticide is typically first combined with the one or more other components of the composition. Combining all the components together may be performed at a manufacturing site, e.g., a manufacturer of a pesticide, such that a pesticide may be provided to an end user pre-formulated. If not already provided to the end-user pre-formulated, a pesticide composition must be prepared, e.g., by an end user. Accordingly, when prepared by an end user, the pesticide composition may be prepared immediately before use or may be prepared ahead of time. For example, a pesticide composition may be prepared within about 0.01 hour to about 10 hours prior to use of the composition, i.e., prior to contacting the composition to a plant, e.g., within about 0.01 hour to about 5 hours, e.g., within about 0.01 hour to about 1.0 hours. Of course, the amount of time a given pesticide may be prepared prior to use may be dictated at least in part on certain limitations of one or more of the components of the composition, where such is typically indicated on instructions for use, e.g., by a respective manufacturer, if applicable. For example, spray mixes that include certain surfactants such as the organosilicone surfactant Silwet L-77 should not sit over 36 hours. Protocols for combining the pesticide composition components together, e.g., as a tank mix, are described above and as such will not be repeated.

Once a pesticide composition is prepared, whether by a manufacturer or by an end user such as a farmer or other agricultural worker, it may then be applied to a plant. A variety of different application protocols may be employed to apply a subject pesticide composition to a plant. Pesticide formulations according to the present invention may be applied as liquids, suspension, emulsions, or solids by conventional application techniques for each. In those embodiments where the pesticide is a commercially available pesticide, the particular application method should follow the application rates suggested by the pesticide manufacturer for the particular pesticide and application method chosen. In general, the application rate of the pesticidally effective formulation of the present invention will deliver a quantity of pesticide sufficient to control the population of a target pest. For example, with insects, the applied insecticide composition should be in a quantity sufficient to cause mortality or render the target insect sterile following consumption or contact. With rodents, the rodenticide composition should be applied in a quantity sufficient to kill or sterilize the rodent following consumption or contact.

In certain embodiments, a pesticide composition may be contacted with the soil. By contact is meant that the composition is introduced into the soil. As such, contact may include spraying so that the composition soaks into the soil, injecting the composition into the soil, flooding the soil with the composition, and the like. In yet other embodiments, the composition may be contacted with at least a portion of the foliage of the plant. By contact in this context is meant that a pesticide composition is placed on the surface of the foliage of the plant(s) to be treated, where the term foliage is used broadly to encompass not only the leaves of the plant, but every other part of the plant that is not underground, i.e. below the soil surface, such that the term foliage includes leaves, stems, flowers, fruit, etc. Contact may be by any convenient method, e.g., via sprayers, dusters, and granular applicators, tank mixers, and the like.

The amount of pesticide composition that is used during any one application will vary greatly depending on the nature of the plant, the particular pesticide composition employed, the environmental conditions, etc., and, as noted, the application rate of the pesticidally effective formulation of the present invention is chosen to deliver a quantity of pesticide sufficient to control the population of a target pest. Where crops are treated with the subject compositions, in certain embodiments the amount that is applied based on acreage may range from about 1 gallon per acre to about 1,000 gallons per acre, e.g., about 5 gallons per acre to about 500 gallons per acre, e.g., about 10 gallons per acre to about 250 gallons per acre. Methods for determining other application rates will be known to those of skill in the art.

Depending on the nature of the plant, the nature of the composition, the targeted pests, and the environmental conditions, as well as other factors, a given pesticide composition may be applied more than once over a given period of time. As such, a given pesticide composition may be applied daily, weekly, every two weeks, monthly etc.

The subject pesticide compositions find use in at least reducing pesticide phytotoxicity of the pesticide present in composition, relative to the pesticide alone or rather not combined as a subject composition. By at least reducing pesticide phytotoxicity is meant that at least one aspect or indicator of phytotoxicity is at least reduced. In certain embodiments, pesticide phytotoxicity may be completely eliminated such that substantially no, including no, effects of phytotoxicity may be observed. The amount of reduction in phytotoxicity accomplished by the subject invention may range from about 1% to about 100% relative to phytotoxicity of the pesticide alone, e.g., from about 5% to about 100%, e.g., from about 20% to about 100%.

As the subject compositions are pesticide compositions, they also find use in pest control. Where the subject compositions are used in pest control, the compositions are used to at least reduce or prevent the undesirable activity of one or more pests with respect to a plant, where this reduction in undesirable activity may be accomplished via a number of different mechanisms, e.g., through death of the pest, through modification of the pest such that it produces reduced amount of toxic agents, etc. The pest(s) that may be targeted by the use of the subject compositions will vary. For example, pests that may be targeted with the subject compositions include, but are not limited to, Lepidopterous pests, such as Peach Twig Borer, Oriental Fruit Moth, Codling Moth, Omnivorous Leafroller, Orange Tortrix, Green Fruitworm, Fruit Tree Leaf Roller, Cankerworm, Cutworm, Navel Orangeworm, Grapeleaf Skeletonizer, Grape Leaffolder, Armyworms, Saltmarsh Caterpillar, Sphinx Moths, Indian Meal Moth, Raisin Moth, American Plum Borer, Prune Limb Borer, Clear-Winged Moths (Sesiidae), Carpenter Moth, and the like; Coleopterous Pests, such as Grape Bud Beetle, Flea Beetle, Branch and Twig Borer, Japanese Beetle, Rose Beetle, Wireworms or Click Beetles (Elateridae), Hoplia Beetle, Western Grape Rootworm, Little Bear Beetle, Darkling Ground Beetle, Dried Fruit Beetle, Sawtoothed Grain Beetle, Southern Pine Beetle (Buprestidae), Longhorn Beetles (Cerambycidae), and the like, etc.

Kits

Also provided by the subject invention are kits. The subject kits may include one or more, including all, components that may be used to prepare a subject pesticide composition. For example, kits may include a pesticide and/or carbon-skeleton energy component and/or a macronutrient component and/or a micronutrient component and/or a vitamin/cofactor component and/or a complexing agent. One or more of the components may already be combined together or pre-formulated. In those embodiments where more than two components are provided in a kit, the pesticide components may already be combined together and as such are packaged in a single container such as a vial, bottle, can, pouch, bag, canister, and the like. In other embodiments, two or more components of a kit may be packaged separately, i.e., not pre-formulated. As such, kits may include one or more separate containers such as vials, can, bottles, pouches, bags, canisters, and the like, each container containing a separate component for a pesticide composition.

Kits may also include one or more other components for use in preparing a pesticide composition in accordance with the subject invention. Accordingly, kits may include one or more of: buffers, surfactants, wetting agents, spreaders, emulsifiers, viscosity regulators, diluents, dispersing agents, foaming agents and foaming suppressants, penetrants, stickers, correctants and attractants, and the like. These components, if provided in a kit, may be provided pre-formulated with one or more other components of the kit, or may be provided in a separate container, e.g., vial, bottle, can, pouch, bag, canister, and the like.

Kits may also include instructions for preparing a pesticide composition, e.g., for combining one or more components to provide a pesticide composition, and/or instructions for applying a prepared pesticide composition to a plant for pest control with at least reduced phytotoxicity as compared to application of a pesticide alone. The instructions may be printed on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic, magnetic or optical storage data file present on a suitable computer readable storage medium, e.g., CD-ROM, diskette, etc. In yet other embodiments, the instructions may not themselves be present in the kit, but means for obtaining the instructions from a remote source, e.g., via the Internet, may be provided. An example of this embodiment is a kit that includes a World Wide Web address where the instructions may be viewed and/or from which the instructions may be downloaded. Some form of access security or identification protocol may be used to limit access to those entitled to use the subject invention.

Experimental

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

I. Phytotoxicity-Mitigating Pesticide Formulations that Include a Carbon Skeleton Energy Component.

Introduction:

In this set of experiments (IA-ID), phytotoxicity mitigating pesticide formulations that include a pesticide and carbon skeleton energy component (sucrose), without a macronutrient component, micronutrient component or vitamin-cofactor component, were contacted with a plant to evaluate the phytotoxicity-mitigating pesticide formulation's ability to mitigate pesticide phytotoxicity.

IA. Mitigation of Insecticide Phytotoxicity

Methods:

In general, tomato plants were contacted with three different treatment formulations: (1) the sodium aluminofluoride insecticide KRYOCIDE with water and surfactant, (2) an insecticide phytotoxicity reducing formulation according to the subject invention, i.e., KRYOCIDE/water/sucrose/surfactant, and (3) sucrose/water. An untreated control was also evaluated.

Protocol:
1) Nine week old potted tomato plants (*Lycopersicon esculentum* var. Celebrity Hybrid, NK)
2) Sodium Aluminofluoride 96% a.i. (KRYOCIDE) made up in a concentration equivalent to 15 lbs per 100 gallons water+Organosilicone Surfactant (Silwet L-77) at 3 oz per 100 gallons
3) KRYOCIDE at 15 lbs per 100 gallons spray mix+SILWET L-77 at 3 oz per 100 gallons spray mix+Sucrose at 25 lbs per 100 gallons spray mix
4) Sucrose at 25 lbs per 100 gallons spray mix+SILWET L-77 at 3 oz per 100 gallons
5) Untreated Control
6) Sprayed to runoff 2× at 5 day intervals
7) Evaluated on day 5 following 2nd spray on 0-10 scale for overall vigor and appearance (0=Poor, 10=Superior)

Results:

| Treatment | Replication 1 | Replication 2 | Replication 3 | Replication 4 | Mean/Statistical Rank |
|---|---|---|---|---|---|
| KRYOCIDE | 6 | 7 | 6 | 6 | 6.25 a |
| KRYOCIDE + Sucrose | 9 | 9 | 9 | 9 | 9.00 b |
| Sucrose | 10 | 9 | 10 | 10 | 9.75 b |
| Control | 8 | 9 | 9 | 9 | 8.75 b |

Key: Treatment means not followed by a common letter are significantly different at the 95% level of confidence Conclusion:

The results show that the KRYOCIDE/sucrose formulation of the subject invention mitigated insecticide phytotoxicity of a tomato plant as the tomato plant contacted with the KRYOCIDE/sucrose formulation of the subject invention showed improved overall vigor and appearance as compared with the KRYOCIDE-contacted plant (i.e., the plant contacted with KRYOCIDE, but not with sucrose) and control plant.

IB. Mitigation of Bactericide-Fungicide Phytotoxicity

Methods:

In general, mung bean plants were contacted with three different treatment formulations: (1) the copper hydroxide bactericide-fungicide KOCIDE with water and surfactant, (2) a bactericide-fungicide phytotoxicity reducing formulation according to the subject invention, i.e., KOCIDE/water/sucrose/surfactant, and (3) sucrose/water. An untreated control was also evaluated.

Protocol:
1) Three week old potted Mung Bean plants (*Phaseolus aureus*)
2) Copper Hydroxide 20% a.i. (KOCIDE) made up in a concentration equivalent to 10 lbs per 100 gallons spray mix+Organosilicone Surfactant (SILWET L-77) at 3 oz per 100 gallons
3) KOCIDE at 10 lbs per 100 gallons spray mix+Sucrose at 25 lbs per 100 gallons+SILWET L-77 at 3 oz per 100 gallons
4) Sucrose at 25 lbs per 100 gallons+SILWET L-77 at 3 oz per 100 gallons
5) Untreated Control
6) Sprayed to runoff 2× at 5 day intervals
7) Evaluated on day 2 following 2nd spray on 0-10 scale for russeting of leaves and overall vigor and appearance (0=Poor, 10=Superior)

Results:

| Treatment | Replication 1 | Replication 2 | Replication 3 | Replication 4 | Mean/Statistical Rank |
|---|---|---|---|---|---|
| KOCIDE | 5 | 6 | 5 | 6 | 5.50 a |
| KOCIDE + Sucrose | 8 | 9 | 8 | 9 | 8.50 b |
| Sucrose | 10 | 10 | 10 | 10 | 10.00 b |
| Control | 9 | 8 | 8 | 9 | 8.50 b |

Key: Treatment means not followed by a common letter are significantly different at the 95% level of confidence Conclusion:

The results show that the KOCIDE/sucrose formulation of the subject invention mitigated bactericide-fungicide induced phytotoxicity of a mung bean plant as the mung bean plant contacted with the KOCIDE/sucrose formulation of the subject invention showed decreased russeting of the leaves and improved overall vigor and appearance as compared with the KOCIDE-contacted plant (i.e., the plant contacted with KOCIDE, but not with sucrose).

IC. Mitigation of Fungicide Phytotoxicity

Methods:

In general, tomato plants were contacted with three different treatment formulations: (1) the clorothalonil fungicide BRAVO WEATHER STIK with water and surfactant, (2) a fungicide phytotoxicity reducing formulation according to the subject invention, i.e., BRAVO WEATHER STIK/water/sucrose/surfactant, and (3) sucrose/water. An untreated control was also evaluated.

Protocol:
1) Seven week old potted tomato plants (*Lycopersicon esculentum* var. Celebrity Hybrid, NK)
2) Clorothalonil 47% a.i. (BRAVO WEATHER STIK) made up in a concentration equivalent to 2 pints per 100 gallons water+Organosilicone Surfactant (SILWET L-77) at 3 oz per 100 gallons
3) BRAVO WEATHER STIK at 2 pints per 100 gallons spray mix+SILWET L-77 at 3 oz per 100 gallons+Sucrose at 25 lbs per 100 gallons
4) Sucrose at 25 lbs per 100 gallons+SILWET L-77 at 3 oz per 100 gallons
5) Untreated Control
6) Sprayed to runoff 2× at 5 day intervals
7) Evaluated on day 5 following 2nd spray on 0-10 scale for overall vigor and appearance (0=Poor, 10=Superior)

Results:

| Treatment | Replication 1 | Replication 2 | Replication 3 | Replication 4 | Mean/Statistical Rank |
|---|---|---|---|---|---|
| BRAVO WS | 5 | 5 | 6 | 5 | 5.25 a |
| BRAVO WS + Sucrose | 9 | 9 | 8 | 8 | 8.50 b |
| Sucrose | 10 | 10 | 10 | 10 | 10.00 b |
| Control | 9 | 9 | 9 | 9 | 9.00 b |

Key: Treatment means not followed by a common letter are significantly different at the 95% level of confidence Conclusion:

The results show that the BRAVO WEATHER STIK/sucrose formulation of the subject invention mitigated fungicide induced phytotoxicity of a tomato plant as the tomato plant contacted with the KRYOCIDE/sucrose formulation of the subject invention showed improved overall vigor and appearance as compared with the BRAVO WEATHER STIK-contacted plant (i.e., the plant contacted with BRAVO WEATHER STIK, but not with sucrose).

ID. Mitigation of Fungicide Phytotoxicity

Methods:

In general, tomato plants were contacted with three different treatment formulations: (1) the propiconazole fungicide ORBIT with water and surfactant, (2) a fungicide phytotoxicity reducing formulation according to the subject invention, i.e., ORBIT/water/sucrose/surfactant, and (3) sucrose/water. An untreated control was also evaluated.

Protocol:

1) Nine week old potted tomato plants (*Lycopersicon esculentum* var. Celebrity Hybrid, NK)
2) Propiconazole 41.8% a.i. (ORBIT) made up in a concentration equivalent to 12 oz per 100 gallons water+Organosilicone Surfactant (SILWET L-77) at 3 oz per 100 gal
3) ORBIT at 12 oz per 100 gallons spray mix+SILWET L-77 at 3 oz per 100 gallons+Sucrose at 25 lbs per 100 gallons
4) Sucrose at 25 lbs per 100 gallons+SILWET L-77 at 3 oz per 100 gallons
5) Untreated Control
6) Sprayed to runoff 2× at 5 day intervals
7) Evaluated on day 5 following 2nd spray on 0-10 scale for overall vigor, leaf distortion and appearance (0=Poor, 10=Superior)

Results:

| Treatment | Replication 1 | Replication 2 | Replication 3 | Replication 4 | Mean/Statistical Rank |
|---|---|---|---|---|---|
| ORBIT | 4 | 5 | 4 | 3 | 4.00 a |
| ORBIT + Sucrose | 8 | 7 | 8 | 7 | 7.50 b |
| Sucrose | 10 | 10 | 10 | 10 | 10.00 c |
| Control | 9 | 9 | 8 | 9 | 8.75 bc |

Key: Treatment means not followed by a common letter are significantly different at the 95% level of confidence Conclusion:

The results show that the ORBIT/sucrose formulation of the subject invention mitigated fungicide induced phytotoxicity of a tomato plant as the tomato plant contacted with the ORBIT/sucrose formulation of the subject invention showed decreased leaf distortion, improved overall vigor and appearance as compared with the ORBIT-contacted plant (i.e., the plant contacted with ORBIT, but not with sucrose).

II. Phytotoxicity-Mitigating Pesticide Formulations that Include a Carbon Skeleton Energy Component, Macronutrient Component, Micronutrient Component and a Vitamin-Cofactor Component.

Introduction:

In this set of experiments (IIA-IID), phytotoxicity mitigating pesticide formulations that include a carbon skeleton energy component, macronutrient component, micronutrient component and a vitamin-cofactor component were contacted with a plant to evaluate the phytotoxicity-mitigating pesticide formulation's ability to mitigate pesticide phytotoxicity. The carbon skeleton energy component, macronutrient component, micronutrient component and a vitamin-cofactor component were provided by the commercially available GREEN THUMB 1-0-2 plant formulation.

IIA. Mitigation of Insecticide Phytotoxicity

Methods:

In these In general, tomato plants were contacted with three different treatment formulations: (1) the sodium aluminofluoride insecticide KRYOCIDE with water and surfactant, (2) an insecticide phytotoxicity reducing formulation according to the subject invention, i.e., KRYOCIDE/water/GREEN THUMB 1-0-2/surfactant, and (3) GREEN THUMB 1-0-2/water. An untreated control was also evaluated.

Protocol:
1) Nine week old potted tomato plants (*Lycopersicon esculentum* var. Celebrity Hybrid, NK)
2) Sodium Aluminofluoride 96% a.i. (KRYOCIDE) made up in a concentration equivalent to 15 lbs per 100 gallons water+Organosilicone Surfactant (SILWET L-77) at 3 oz per 100 gallons
3) Kryocide at 15 lbs per 100 gallons spray mix+SILWET L-77 at 3 oz per 100 gallons spray mix+GREEN THUMB 102 (commercially available carbon-based foliar nutrient composition containing: a) Carbon-Skeleton/Energy Component, b) Macronutrient Component, c) Micronutrient Component, d) Vitamin-Cofactor Component at 4 gal per 100 gallons spray mix
4) GREEN THUMB 102 at 4 gallons per 100 gallons+ SILWET L-77 at 3 oz per 100 gallons
5) Untreated Control
6) Sprayed to runoff 2× at 5 day intervals
7) Evaluated on day 5 following 2nd spray on 0-10 scale for overall vigor and appearance (0=Poor, 10=Superior)

Results:

| Treatment | Replication 1 | Replication 2 | Replication 3 | Replication 4 | Mean/Statistical Rank |
|---|---|---|---|---|---|
| KRYOCIDE | 7 | 5 | 6 | 5 | 5.75 a |
| KRYOCIDE + GREEN THUMB 102 | 10 | 10 | 10 | 10 | 10.00 b |
| GREEN THUMB 102 | 10 | 10 | 10 | 10 | 10.00 b |
| Control | 8 | 8 | 9 | 9 | 8.50 b |

Key: Treatment means not followed by a common letter are significantly different at the 95% level of confidence Conclusion:

The results show that the KRYOCIDE/GREEN THUMB 102 formulation of the subject invention mitigated insecticide phytotoxicity of a tomato plant as the tomato plant contacted with the KRYOCIDE/GREEN THUMB 102 formulation of the subject invention showed improved overall vigor and appearance as compared with the KRYOCIDE-contacted plant (i.e., the plant contacted with BRAVO WEATHER STIK, but not with GREEN THUMB 102) and control plant and showed analogous results to the plant contacted solely with the GREEN THUMB 102, i.e., not contacted with pesticide at all.

IIB. Mitigation of Bactericide-Fungicide Phytotoxicity

Methods:

In general, mung bean plants were contacted with three different treatment formulations: (1) the copper hydroxide bactericide-fungicide KOCIDE with water and surfactant, (2) a bactericide-fungicide phytotoxicity reducing formulation according to the subject invention, i.e., KOCIDE/water/GREEN THUMB 102/surfactant, and (3) GREEN THUMB 102/water. An untreated control was also evaluated.

Protocol:
1) Three week old potted Mung Bean plants (*Phaseolus aureus*)
2) Copper Hydroxide 20% a.i. (KOCIDE) made up in a concentration equivalent to 10 lbs per 100 gallons+Organosilicone Surfactant (SILWET L-77) at 3 oz per 100 gallons
3) KOCIDE at 10 lbs per 100 gallons spray mix+GREEN THUMB 102 at 4 gallons per 100 gallons+Silwet L-77 at 3 oz per 100 gallons
4) GREEN THUMB 102 at 4 gallons per 100 gallons+ SILWET L-77 at 3 oz per 100 gallons
5) Untreated Control
6) Sprayed to runoff 2× at 5 day intervals
7) Evaluated on day 2 following 2nd spray on 0-10 scale for russeting of leaves and overall vigor and appearance (0=Poor, 10=Superior)

Results:

| Treatment | Replication 1 | Replication 2 | Replication 3 | Replication 4 | Mean/Statistical Rank |
|---|---|---|---|---|---|
| KOCIDE | 5 | 5 | 5 | 6 | 5.25 a |
| KOCIDE + GREEN THUMB 102 | 9 | 10 | 10 | 10 | 9.75 b |
| GREEN THUMB 102 | 10 | 10 | 10 | 10 | 10.00 b |
| Control | 8 | 8 | 8 | 9 | 8.25 b |

Key: Treatment means not followed by a common letter are significantly different at the 95% level of confidence Conclusion:

The results show that the KOCIDE/GREEN THUMB 102 formulation of the subject invention mitigated bactericide-fungicide induced phytotoxicity of a mung bean plant as the mung bean plant contacted with the KOCIDE/GREEN THUMB 102 formulation of the subject invention showed decreased russeting of the leaves and improved overall vigor and appearance as compared with the KOCIDE-contacted plant (i.e., the plant contacted with KOCIDE, but not with GREEN THUMB 102) and the control.

IIC. Mitigation of Fungicide Phytotoxicity

Methods:

In general, tomato plants were contacted with three different treatment formulations: (1) the clorothalonil fungicide BRAVO WEATHER STIK with water and surfactant, (2) a fungicide phytotoxicity reducing formulation according to the subject invention, i.e., BRAVO WEATHER STIK/water/GREEN THUMB 102/surfactant, and (3) GREEN THUMB 102/water. An untreated control was also evaluated.

Protocol:
1) Seven week old potted tomato plants (*Lycopersicon esculentum* var. Celebrity Hybrid, NK)
2) Clorothalonil 47% a.i. (BRAVO WEATHER STIK) made up in a concentration equivalent to 2 pints per 100 gallons water+Organosilicone Surfactant (SILWET L-77) at 3 oz per 100 gallons
3) Bravo WS at 2 pints per 100 gallons pray mix+SILWET L-77 at 3 oz per 100 gallons+GREEN THUMB 102 at 4 gallons per 100 gallons
4) GREEN THUMB 102 at 4 gallons per 100 gal+SILWET L-77 at 3 oz per 100 gallons
5) Untreated Control
6) Sprayed to runoff 2× at 5 day intervals
7) Evaluated on day 5 following 2nd spray on 0-10 scale for overall vigor and appearance (0=Poor, 10=Superior)

Results:

| Treatment | Replication 1 | Replication 2 | Replication 3 | Replication 4 | Mean/Statistical Rank |
|---|---|---|---|---|---|
| BRAVO WS | 5 | 4 | 5 | 6 | 5.00 a |
| BRAVO WS + GREEN THUMB 102 | 10 | 10 | 10 | 9 | 9.75 b |
| GREEN THUMB 102 | 10 | 10 | 10 | 10 | 10.00 b |
| Control | 9 | 8 | 9 | 9 | 8.75 b |

Key: Treatment means not followed by a common letter are significantly different at the 95% level of confidence Conclusion:

The results show that the BRAVO WEATHER STIK/GREEN THUMB 102 formulation of the subject invention mitigated fungicide induced phytotoxicity of a tomato plant as the tomato plant contacted with the KRYOCIDE/GREEN THUMB 102 formulation of the subject invention showed improved overall vigor and appearance as compared with the BRAVO WEATHER STIK-contacted plant (i.e., the plant contacted with BRAVO WEATHER STIK, but not with GREEN THUMB 102) and the control.

IID. Mitigation of Fungicide Phytotoxicity

Methods:

In general, tomato plants were contacted with three different treatment formulations: (1) the propiconazole fungicide ORBIT with water and surfactant, (2) a fungicide phytotoxicity reducing formulation according to the subject invention, i.e., ORBIT/water/GREEN THUMB 102/surfactant, and (3) GREEN THUMB 102/water. An untreated control was also evaluated.

Protocol:
1) Nine week old potted tomato plants (*Lycopersicon esculentum* var. Celebrity Hybrid, NK)
2) Propiconazole 41.8% a.i. (ORBIT) made up in a concentration equivalent to 12 oz per 100 gallons water+Organosilicone Surfactant (SILWET L-77) at 3 oz per 100 gallons
3) ORBIT at 12 oz per 100 gallons spray mix+Silwet L-77 at 3 oz per 100 gallons+GREEN THUMB 102 at 4 gallons per 100 gallons spray mix
4) GREEN THUMB 102 at 4 gallons per 100 gallons+SILWET L-77 at 3 oz per 100 gallons
5) Untreated Control
6) Sprayed to runoff 2× at 5 day intervals
7) Evaluated on day 5 following 2nd spray on 0-10 scale for overall vigor, leaf distortion and appearance (0=Poor, 10=Superior)

Results:

| Treatment | Replication 1 | Replication 2 | Replication 3 | Replication 4 | Mean/Statistical Rank |
|---|---|---|---|---|---|
| ORBIT | 4 | 4 | 4 | 4 | 4.00 a |
| ORBIT + GREEN THUMB 102 | 9 | 9 | 9 | 9 | 9.00 b |
| GREEN THUMB 102 | 10 | 10 | 10 | 10 | 10.00 b |
| Control | 8 | 9 | 8 | 9 | 8.50 b |

Key: Treatment means not followed by a common letter are significantly different at the 95% level of confidence Conclusion:

The results show that the ORBIT/GREEN THUMB 102 formulation of the subject invention mitigated fungicide induced phytotoxicity of a tomato plant as the tomato plant contacted with the ORBIT/GREEN THUMB 102 formulation of the subject invention showed decreased leaf distortion, improved overall vigor and appearance as compared with the ORBIT-contacted plant (i.e., the plant contacted with ORBIT, but not with GREEN THUMB 102) and the control.

It is evident from the above results and discussion that improved pesticide compositions that find use in a variety of agricultural applications are provided. The compositions are relatively simple and easy to produce and use. Despite their simplicity to prepare and use, the compositions can provide for significant improvement in terms of at least reduced pesticide phytotoxicity, e.g., improved plant health and the like as compared with the application of a pesticide alone (i.e., a pesticide not combined as a subject composition). As such, the subject compositions are a significant advance in the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. An aqueous pesticide composition for applying to a plant, the composition consisting of:
    (a) a phytotoxicity-inducing amount of about 0.01% to about 15% w/w of a phytotoxicity-inducing synthetic pesticide selected from a sodium aluminofluoride pesticide, a copper hydroxide pesticide, a chlorothalonil pesticide, and a propiconazole pesticide; and
    (b) a pesticide-induced phytotoxicity reducing component comprising:
        (i) about 0.1% to about 20% w/w of an assimilable carbon-skeleton energy component comprising corn syrup;
        (ii) about 0.0001% to about 0.5% w/w of a water soluble macronutrient component comprising N, K, Ca and Mg;
        (iii) about 0.00000001% to about 0.1% w/w of a water soluble micronutrient component comprising Zn, Fe and Mn;
        (iv) about 0.0000001% to about 0.1% w/w of a vitamin/cofactor component comprising three or more vitamin/cofactors selected from the group consisting of pyridoxine, cyanocobalamin, thiamine, pyrophosphate, riboflavin, biotin, pantothenic acid, phosphatidylcholine, inositol, para-aminobenzoic acid (PABA), nicotinic acid and folic acid; and
        (v) an organosilicone surfactant;
    wherein components (i), (ii), (iii), (iv) and (v) are present in amounts sufficient to reduce pesticide-induced phytotoxicity of the plant.

2. The pesticide composition of claim 1 wherein said phytotoxicity-inducing synthetic pesticide is a sodium aluminofluoride pesticide.

3. The pesticide composition of claim 1 wherein said phytotoxicity-inducing synthetic pesticide is a copper hydroxide pesticide.

4. The pesticide composition of claim 1 wherein said phytotoxicity-inducing synthetic pesticide is a chlorothalonil pesticide.

5. The pesticide composition of claim 1 wherein said phytotoxicity-inducing synthetic pesticide is a propiconazole pesticide.

6. A method comprising applying a pesticide composition according to claim 1 to a plant.

7. The method of claim 6, wherein said method results in a reduction of the phytotoxicity of said pesticide.

8. An aqueous pesticide composition for applying to a plant, the composition consisting of:
    (a) a phytotoxicity-inducing amount of about 0.01% to about 15% w/w of a phytotoxicity-inducing synthetic pesticide selected from a sodium aluminofluoride pesticide, a copper hydroxide pesticide, a chlorothalonil pesticide, and a propiconazole pesticide; and
    (b) a pesticide-induced phytotoxicity reducing component comprising:
        (i) about 0.1% to about 20% w/w of an assimilable carbon-skeleton energy component comprising corn syrup;
        (ii) about 0.0001% to about 0.5% w/w of a water soluble macronutrient component comprising N, K, Ca and Mg;
        (iii) about 0.00000001% to about 0.1% w/w of a water soluble micronutrient component comprising Zn, Fe and Mn;
        (iv) about 0.0000001% to about 0.1% w/w of a vitamin/cofactor component comprising three or more vitamin/cofactors selected from the group consisting of pyridoxine, cyanocobalamin, thiamine, pyrophosphate, riboflavin, biotin, pantothenic acid, phosphatidylcholine, inositol, para-aminobenzoic acid (PABA), nicotinic acid and folic acid,
        (v) about 0.01% to about 30% w/w of a complexing agent component comprising one or more of citric acid and fulvic acid; and
        (vi) an organosilicone surfactant,
    wherein components (i), (ii), (iii), (iv), (v) and (vi) are present in amounts sufficient to reduce pesticide-induced phytotoxicity of the plant.

9. The pesticide composition of claim 8 wherein said phytotoxicity-inducing synthetic pesticide is a sodium aluminofluoride pesticide.

10. The pesticide composition of claim 8 wherein said phytotoxicity-inducing synthetic pesticide is a copper hydroxide pesticide.

11. The pesticide composition of claim 8 wherein said phytotoxicity-inducing synthetic pesticide is a chlorothalonil pesticide.

12. The pesticide composition of claim 8 wherein said phytotoxicity-inducing synthetic pesticide is a propiconazole pesticide.

13. A method comprising applying a pesticide composition according to claim 8 to a plant.

14. The method of claim 13, wherein said method results in a reduction of the phytotoxicity of said pesticide.

* * * * *

UNITED STATES PATENT AND TRADEMARK OFFICE
CERTIFICATE OF CORRECTION

| | | |
|---|---|---|
| PATENT NO. | : 7,927,616 B2 | |
| APPLICATION NO. | : 10/759788 | |
| DATED | : April 19, 2011 | |
| INVENTOR(S) | : Thomas T. Yamashita | |

It is certified that error appears in the above-identified patent and that said Letters Patent is hereby corrected as shown below:

Col. 4, Line 59, insert the following paragraph:

--[0001] Table 1 provides exemplary pesticides that may be used in the subject invention. However, such is for exemplary purposes only and is in no way intended to limit the scope of the invention.--

Signed and Sealed this
First Day of November, 2011

David J. Kappos
*Director of the United States Patent and Trademark Office*